(12) United States Patent
Pratt

(10) Patent No.: US 6,966,587 B1
(45) Date of Patent: Nov. 22, 2005

(54) SELF-EMPTYING BAILER

(76) Inventor: David W. Pratt, 3080 Belcher Rd., Palm Harbor, FL (US) 34683

( * ) Notice: Subject to any disclaimer, the term of this patent is extended or adjusted under 35 U.S.C. 154(b) by 0 days.

(21) Appl. No.: 10/711,351

(22) Filed: Sep. 13, 2004

(51) Int. Cl.[7] .............................................. G01N 1/12
(52) U.S. Cl. ............................. 294/68.22; 73/864.63; 251/333
(58) Field of Search ................ 294/68.22, 68.25; 73/864.63, 864.65; 137/533.11, 533.13, 533.15; 251/333

(56) References Cited

U.S. PATENT DOCUMENTS

| | | | |
|---|---|---|---|
| 348,960 A | * | 9/1886 | Foster ...................... 294/68.25 |
| 686,951 A | * | 11/1901 | Plotts ......................... 166/165 |
| 1,875,174 A | * | 8/1932 | McGivern ................ 294/68.25 |

* cited by examiner

Primary Examiner—Dean J. Kramer
(74) Attorney, Agent, or Firm—Smith & Hopen, P.A.; Ronald E. Smith

(57) ABSTRACT

A bailer has a check valve housing at its leading end. A free-floating ball in the check valve housing is unseated and admits liquid fluid into the bailer as the bailer enters a body of liquid fluid. The free-floating ball is seated and seals the liquid fluid within the check valve housing against leakage when the bailer is retrieved from the body of liquid fluid. An annular valve seat is formed flush with a leading edge of the check valve housing and the free-floating ball has a diameter only slightly greater than the diameter of the annular valve seat. About half of the free-floating ball extends downwardly from the check valve housing. The structure prevents formation of an annular air pocket at the leading end of the check valve housing so that liquid fluid drained from the bailer is not contaminated by oxygen.

2 Claims, 2 Drawing Sheets

SELF-EMPTYING BAILER

BACKGROUND OF INVENTION

1. Field of the Invention

This invention relates, generally, to bailers. More particularly, it relates to a bailer that is bottom-emptied to avoid contamination by oxygen.

2. Description of the Prior Art

U.S. pending patent application Ser. No. 10/707,291 discloses ball valve positioned within a tapered check valve seat positioned at the leading end of a bailer. When the ball valve is fully seated within the valve seat formed on an interior surface of the valve housing, liquid fluid within the hollow interior of the bailer is sealed within said hollow interior. When the ball valve is unseated from the valve seat, liquid fluid within the hollow interior of the bailer flows past the unseated ball valve and into a container positioned below the check valve seat to collect the liquid fluid.

Bailers are best emptied from the bottom because unacceptable amounts of oxygen are introduced into the sample if the bailer is decanted from the top.

The ball valve of the co-pending patent application depends at least to some extent from the bottom of the bailer. Accordingly, placing the bailer on a flat surface drives the ball valve upwardly into the valve housing so that the liquid fluid content of the bailer begins flowing out.

However, oxygen is introduced into the liquid fluid as it flows out of the bailer into a capturing device because the valve seat upon which the ball valve sits is spaced sufficiently far from the bottom of the check valve housing to form an annular air pocket around the ball valve. The oxygen in the air mixes with the liquid fluid content of the bailer during the emptying process, producing a false reading of the oxygen content of the liquid fluid.

An improved ball valve is therefore needed. The improved ball valve would substantially eliminate all oxygen contact with the liquid fluid as said liquid fluid is emptied from the bottom of the check valve.

However, in view of the prior art considered as a whole at the time the present invention was made, it was not obvious to those of ordinary skill in the pertinent art how the art could be advanced to provide a bottom-emptying bailer having a ball valve that eliminates oxygen entry into the liquid at the time of bailer decanting.

SUMMARY OF THE INVENTION

The long-standing but heretofore unfulfilled need for a bottom-emptying bailer having a ball valve that serves as a check valve that prevents oxygen from contacting liquid fluid drained from the bailer during a bottom-emptying procedure is now met by a new, useful, and nonobvious invention.

The novel bailer valve housing includes a cylindrical trailing end adapted for engagement with a cylindrical main body of a bailer. The valve housing has a leading end with tapered sidewalls. A ball valve is disposed in the valve housing and an annular valve seat is formed in the leading end. The annular valve seat is formed flush with a leading edge of the leading end and the ball valve has a diameter only slightly greater than a diameter of the annular valve seat.

Accordingly, about half of the ball valve extends downwardly from the leading edge of the valve housing. Liquid fluid in the valve housing is therefore captured within the valve housing when the ball valve is fully seated in the annular valve seat. The liquid fluid captured within the valve housing occupies all of the valve housing. More specifically, the liquid fluid wets the part of the ball valve that is in inside the valve housing and the liquid fluid is flush with the leading edge of the valve housing. This prevents formation of an air pocket between the liquid fluid and the leading edge of the valve housing.

The liquid fluid is drained from the valve housing when the ball valve is unseated from the annular check valve. The liquid fluid does not encounter oxygen during the draining process because the flush positioning of the annular valve seat with the leading edge of the valve housing prevents formation of an air pocket at the leading edge.

An important advantage of this invention is that it prevents oxygen from contacting the liquid fluid drained from the bottom of a bailer.

Another important advantage is that is enables the bailer to be emptied by positioning the leading end of the valve housing on a flat surface, thereby eliminating the need for hand-held bottom-emptying devices.

Further important advantages and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
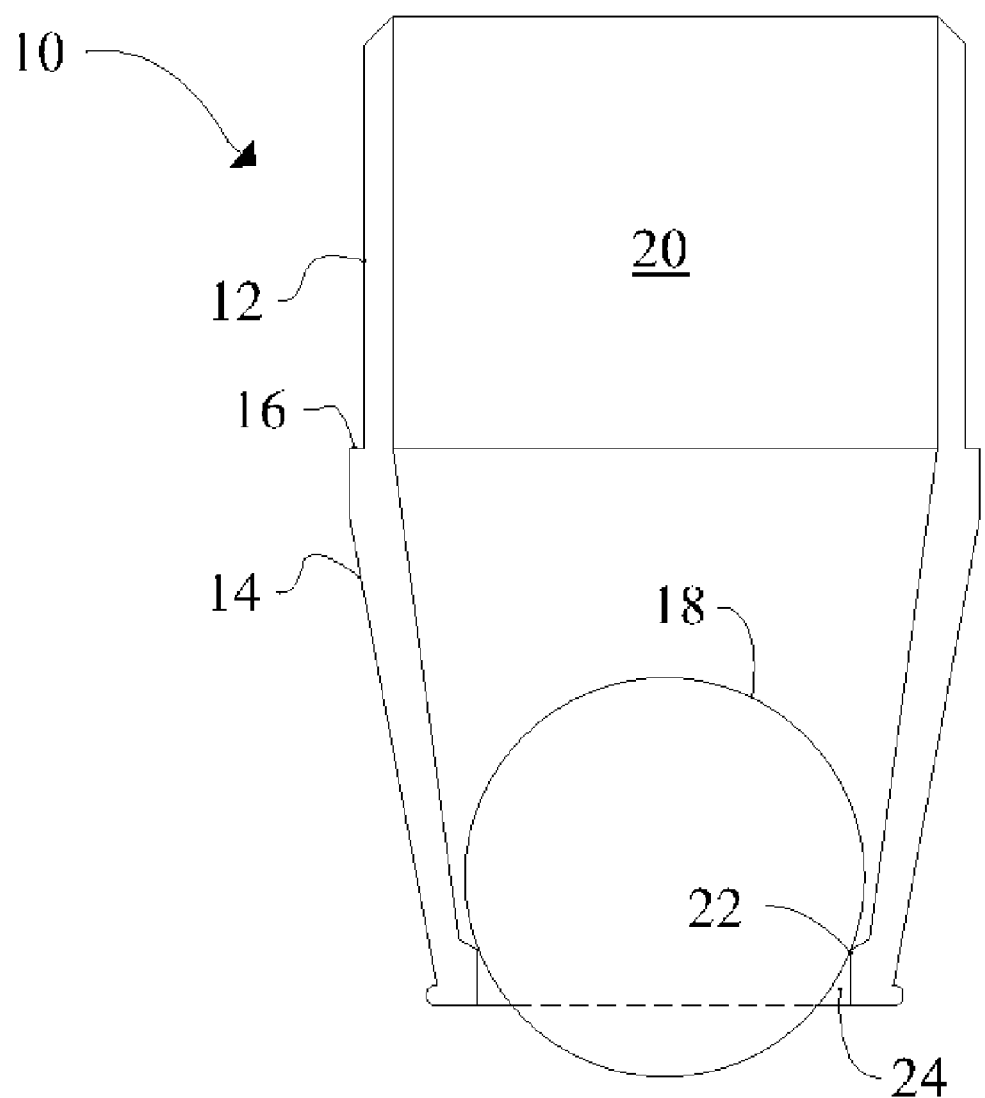
FIG. 1 is a longitudinal sectional view of a prior art valve housing.

Referring now to FIG. 1, there it will be seen that a prior art valve housing is denoted as a whole by the reference numeral 10.

Valve housing 10 has a cylindrical trailing part 12 and a leading end 14 having tapered sidewalls. Annular shoulder 16 is formed where cylindrical trailing part 12 meets leading end 14. It should be understood that cylindrical trailing part 12 is slidingly received within a cylindrical main body of a bailer, not depicted, and that shoulder 16 provides a stop means that limits insertion of valve body 10 into said hollow interior.

Ball valve 18 is a check valve. It is unseated to admit liquid fluid into the hollow interior 20 of valve housing 10 and hence into the undepicted hollow interior of the bailer when the bailer enters into liquid fluid. Ball valve 18 is seated on annular valve seat 22 to prevent leakage of liquid fluid from said hollow interior when the bailer is retrieved from the liquid fluid.

Annular air pocket 24 is formed at the leading end of valve housing 10. The oxygen in this air pocket contaminates the liquid content of the bailer when ball valve 18 is unseated from valve seat 22.

Figure 2:
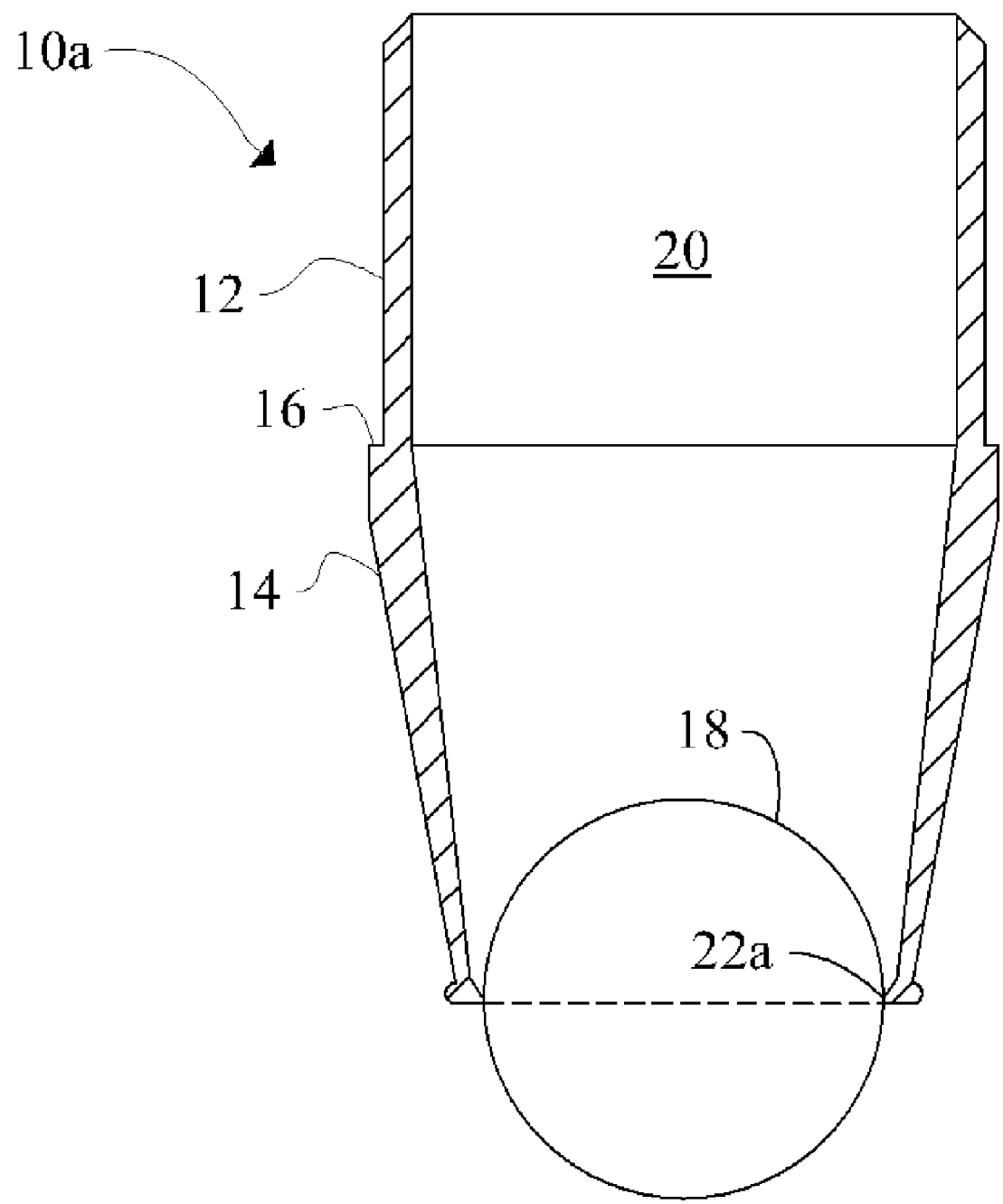
FIG. 2 is a longitudinal sectional view of the novel valve housing.

Novel valve housing 10a is depicted in FIG. 2. As in the prior art structure of FIG. 1, novel valve housing 10a includes cylindrical trailing part 12 and a leading end 14 having tapered sidewalls. Annular shoulder 16 is formed where cylindrical trailing part 12 meets leading end 14.

Ball valve 18 is a check valve. It is unseated to admit liquid fluid into the hollow interior 20 of valve housing 10 and hence into the undepicted hollow interior of the bailer when the bailer enters into liquid fluid. Ball valve 18 is seated on annular valve seat 22a to prevent leakage of liquid fluid from said hollow interior when the bailer is retrieved from the liquid fluid.

Significantly, annular valve seat 22a is positioned flush with the leading end of valve housing 10a and the diameter of ball 18 is made only slightly greater than the diameter of valve seat 22a so that the lower half of ball 18 extends downwardly from the leading edge of said valve housing. Valve seat 22a has a wedge shape when seen in section as depicted in FIG. 2. It extends radially inwardly from the leading edge of leading end 14 and decreases in width from a relatively wide radially outermost end to a point-like radially innermost end that contacts ball 18, forming a thin annular contact about the circumference of said ball valve 18. Annular air space 24 in the prior art valve housing is therefore eliminated in the novel valve housing. Accordingly, when ball valve 18 is pressed against a flat table top or other flat barrier, liquid within the hollow interior of the bailer is drained therefrom without contacting said annular air pocket and thus is not contaminated with oxygen.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A bailer valve housing, comprising:
    a cylindrical trailing end adapted for engagement with a cylindrical main body of a bailer;
    said valve housing having a leading end with tapered sidewalls;
    a ball valve disposed in said valve housing;
    an annular valve seat formed in said leading end;
    said ball valve adapted to be lifted from said annular valve seat by inflowing liquid fluid when said bailer is lowered into a body of liquid fluid so that said inflowing liquid fluid enters the bailer from a leading, bottom end thereof;
    said annular valve seat formed flush with a leading edge of said leading end;
    said annular valve seat having a wedge shape that extends radially inwardly from said leading edge, said wedge shape reducing in width from a relatively wide base at its radially outermost end to a point-like radially innermost end, thereby forming a thin annular contact with said ball valve;
    said ball valve having a diameter only slightly greater than a diameter of said annular valve seat;
    about half of said ball valve extending downwardly from said leading edge of said valve housing;
    whereby liquid fluid in said valve housing is captured within said valve housing when said ball valve is fully seated in said annular valve seat;
    whereby said liquid fluid captured within said valve housing occupies all of said valve housing, being flush with said leading end of said valve housing so that no air pocket is formed between said liquid fluid and said leading end;
    whereby said liquid fluid is drained from said valve housing when said ball valve is unseated from said annular valve seat;
    whereby said liquid fluid does not encounter oxygen during said draining because the flush positioning of said annular valve seat with the leading edge of said valve housing prevents formation of an annular air pocket at said leading edge and;
    whereby oxygenation of said liquid fluid is minimized by said inflow of liquid fluid into said bailer from said bottom end of said bailer.

2. The bailer of claim 1, further comprising:
    said ball valve having a spherical configuration.

\* \* \* \* \*